United States Patent
Harada et al.

(10) Patent No.: US 11,596,936 B2
(45) Date of Patent: Mar. 7, 2023

(54) METHOD FOR REGENERATING CATALYST AND METHOD FOR PRODUCING CARBONATE ESTER

(71) Applicant: MITSUBISHI GAS CHEMICAL COMPANY, INC., Tokyo (JP)

(72) Inventors: Hidefumi Harada, Tokyo (JP); Takehiko Isobe, Tokyo (JP); Hongyu Liu, Tokyo (JP); Yousuke Shinkai, Tokyo (JP); Ryotaro Umezu, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 306 days.

(21) Appl. No.: 16/649,831

(22) PCT Filed: Sep. 25, 2018

(86) PCT No.: PCT/JP2018/035250
§ 371 (c)(1),
(2) Date: Mar. 23, 2020

(87) PCT Pub. No.: WO2019/065549
PCT Pub. Date: Apr. 4, 2019

(65) Prior Publication Data
US 2020/0282389 A1    Sep. 10, 2020

(30) Foreign Application Priority Data
Sep. 29, 2017   (JP) .............................. JP2017-191114

(51) Int. Cl.
*B01J 38/52*    (2006.01)
*B01J 23/92*    (2006.01)
*C07C 68/04*    (2006.01)

(52) U.S. Cl.
CPC ............... *B01J 38/52* (2013.01); *B01J 23/92* (2013.01); *C07C 68/04* (2013.01)

(58) Field of Classification Search
CPC ............ B01J 38/52; B01J 23/92; C07C 68/04
USPC ........................................................ 558/260
See application file for complete search history.

(56) References Cited

U.S. PATENT DOCUMENTS

2002/0198397 A1   12/2002  Yoshisato

FOREIGN PATENT DOCUMENTS

| JP | 2010-77113 | 4/2010 |
| JP | 2012-162523 | 8/2012 |
| WO | 99/06142 | 2/1999 |
| WO | 2015/099053 | 7/2015 |
| WO | 2019/138993 A1 | 7/2019 |

OTHER PUBLICATIONS

Bansode, Atul et al., "Continuous DMC Synthesis from CO2 and Methanol over a CeO2 Catalyst in a Fixed Bed Reactor in the Presence of a Dehydrating Agent", ACS Catalysis, 2014, pp. 3877-3880.
Honda, Masayoshi et al., "Ceria-Catalyzed Conversion of Carbon Dioxide into Dimethyl Carbonate with 2-Cyanopyridine", ChemSusChem, 6, 2013, pp. 1341-1344.
Stoian, Dragos et al., "Catalysis under microscope: Unraveling the mechanism of catalyst de- and re-activation in the continuous dimethyl carbonate synthesis from CO2 and methanol in the presence of a dehydrating agent", Catalysis Today vol. 283, 2017, pp. 2-10.
Nakagawa, Yoshinao et al., "Synthesis of dimethyl carbonate from carbon dioxide and methanol by means of cera catalyst in which nitrile is used as dehydrating-agent", Proceedings for forum a of 110th Catalysis Society of Japan Meeting, 2012, pp. 145-146 (partial translation).
Official Communication (ISR) dated Dec. 18, 2018 in International Patent Application No. PCT/JP2018/035250.
Extended European Search Report issued in European Patent Application No. 18861510.8 dated Oct. 7, 2020.

*Primary Examiner* — Kristin A Vajda
(74) *Attorney, Agent, or Firm* — Greenblum & Bernstein, P.L.C.

(57) ABSTRACT

Realized is a method for restoring the activity of a catalyst for producing a carbonate ester by a simple technique with no use of a complicated step such as calcining or the like to allow the catalyst to be reusable, and a method for producing a carbonate ester at a high yield by use of the catalyst thus regenerated. The above-described problem has been solved by a method for regenerating a catalyst containing $CeO_2$, the catalyst being usable for a carbonate ester generation reaction of generating a carbonate ester from carbon dioxide and an alcohol, the method comprising (a) a separation step of separating the catalyst as a crude catalyst from a reaction solution of carbon dioxide and the alcohol; and (b) a catalyst processing step of washing the crude catalyst with a washing alcohol to provide a purified catalyst.

14 Claims, 2 Drawing Sheets

METHOD FOR REGENERATING CATALYST AND METHOD FOR PRODUCING CARBONATE ESTER

TECHNICAL FIELD

The present invention relates to a method for regenerating a catalyst, specifically, to a method for regenerating a catalyst usable to generate a carbonate ester, and a method for producing the carbonate ester.

BACKGROUND ART

"Carbonate ester" is a generic name of a compound obtained as a result of one atom or two atoms among two hydrogen atoms of carbonic acid. $CO(OH)_2$, being substituted with an alkyl group or an aryl group, and has a structure of RO—C(=O)—OR' (R and R' each represent a saturated hydrocarbon group or an unsaturated hydrocarbon group).

A carbonate ester is used as an additive such as a gasoline additive for improving the octane value, a diesel fuel additive for decreasing the amount of particles in exhaust gas, or the like. A carbonate ester is also used as, for example, an alkylation agent, a carbonylation agent, a solvent or the like for synthesizing resins or organic compounds such as polycarbonate, urethane, pharmaceutical drugs, agricultural chemicals or the like, a material of an electrolytic solution of lithium ion cells, a material of lubricant oil, or a material of an oxygen absorber for rust inhibition of boiler pipes. As can be seen, a carbonate ester is a very useful compound.

According to a known method for producing a carbonate ester, a carbonate ester is directly synthesized from an alcohol and carbon dioxide using a heterogeneous catalyst. For example, according to a known reaction, an alcohol and carbon dioxide are reacted with each other under the presence of a hydration agent that removes water as a by-product from the reaction system, and as a result, a carbonate ester is generated. For such a carbonate ester generation reaction, a solid catalyst containing $CeO_2$ (cerium oxide) or the like may be used (see Patent Documents 1 through 3 and Non-patent Documents 1 and 2).

These prior art documents disclose baking a catalyst to be regenerated. However, baking a catalyst requires a large-scale device, a long processing time and high cost, which prevents efficient production of a carbonate ester.

It is also known to wash a catalyst in order to produce a carbonate ester (see Non-patent Document 3). However, it is difficult to fully restore the reactivity of the catalyst by such a method.

CITATION LIST

Patent Literature

Patent Document 1: Japanese Laid-Open Patent Publication No. 2012-162523
Patent Document 2: Japanese Laid-Open Patent Publication No. 2010-77113
Patent Document 3: WO2015/099053

Non-Patent Literature

Non-patent Document 1: ACS Catal., 2014, 4(11), pp. 3877-3880
Non-patent Document 2: ChemSusChem 2013, 6, pp. 1341-1344
Non-patent Document 3: Catalysis Today Volume 283, pp. 2-10

SUMMARY OF INVENTION

Technical Problem

In light of the above-described technological problems, an object of the present invention is to realize a method for restoring the activity of a catalyst for producing a carbonate ester by a simple technique with no use of a complicated step such as calcining or the like to allow the catalyst to be reusable, and a method for producing a carbonate ester at a high yield by use of the catalyst thus regenerated.

Solution to Problem

In order to solve the above-described problems, the present inventors made studies on, for example, a method by which a catalyst for producing a carbonate ester is separated from a reaction system and washed and purified to regenerate the catalyst. As a result of studying conditions under which the catalyst for producing a carbonate ester is washed as described above, the present inventors have found that the activity of a catalyst may be restored by a simple method of using a predetermined washing agent. The gist of the present invention is as follows.

(1) A method for regenerating a catalyst containing $CeO_2$, the catalyst being usable for a carbonate ester generation reaction of generating a carbonate ester from carbon dioxide and an alcohol, the method comprising:
  (a) a separation step of separating the catalyst as a crude catalyst from a reaction solution of carbon dioxide and the alcohol, and
  (b) a catalyst processing step of washing the crude catalyst with a washing alcohol to provide a purified catalyst.

(2) The method for regenerating a catalyst according to (1) above, wherein the catalyst has an average particle diameter of 0.01 to 200 μm.

(3) The method for regenerating a catalyst according to (1) or (2) above, wherein the catalyst has a specific surface area of 50 to 200 $m^2/g$.

(4) The method for regenerating a catalyst according to any one of (1) through (3) above, wherein the washing alcohol contains an alcohol of the same type as the alcohol used for the carbonate ester generation reaction.

(5) The method for regenerating a catalyst according to any one of (1) through (4) above, wherein the washing alcohol contains an alcohol having a carbon number of 1 to 4.

(6) The method for regenerating a catalyst according to (5) above, wherein the washing alcohol contains at least one of propanol and butanol.

(7) The method for regenerating a catalyst according to any one of (1) through (6) above, further comprising (c) a recovery step of recovering the washing alcohol used to wash the crude catalyst, wherein the recovered washing alcohol is used for the carbonate ester generation reaction.

(8) The method for regenerating a catalyst according to any one of (1) through (7) above, wherein in (b) the catalyst processing step, the crude catalyst is washed at 0 to 150° C.

(9) The method for regenerating a catalyst according to (8) above, wherein in (b) the catalyst processing step, the crude catalyst is washed at room temperature.

(10) The method for regenerating a catalyst according to any one of (1) through (9) above, wherein in (b) the catalyst processing step, the washing alcohol is of a molar ratio of 1.5 to 10000 with respect to the crude catalyst to be washed.

(11) The method for regenerating a catalyst according to any one of (1) through (10) above, wherein in (b) the catalyst processing step, the crude catalyst is washed for a time period in the range of 1 second to 600 minutes.

(12) The method for regenerating a catalyst according to any one of (1) through (11) above, wherein (b) the catalyst processing step further includes a step of calcining the washed crude catalyst.

(13) A method for producing a carbonate ester, the method using the purified catalyst, regenerated by the method for regenerating a catalyst according to any one of (1) through (12) above, for a carbonate ester generation reaction of generating a carbonate ester from carbon dioxide and an alcohol.

(14) The method for producing a carbonate ester according to (13) above, further comprising:

(e) a hydration step of hydrating an aromatic nitrile compound with water generated in the carbonate ester generation reaction to generate an aromatic amide compound; and (f) a regeneration step of dehydrating the aromatic amide compound to regenerate the aromatic nitrile compound.

(15) The method for producing a carbonate ester according to (13) or (14) above, wherein the method uses no solvent.

Advantageous Effects of Invention

According to the present invention described above, the activity of a catalyst may be fully restored by a simple method of washing the catalyst used to produce a carbonate ester with an alcohol for washing, and thus the catalyst is made reusable. Also according to the present invention, as described below in detail, in the case where, for example, the type of the alcohol for washing and the type of the alcohol to be used to produce the carbonate ester are adjusted, the yield of the carbonate ester may be improved and the steps for producing the carbonate ester may be simplified.

As described above, according to a method for regenerating a catalyst of the present invention, a method for producing a carbonate ester efficiently may also be realized.

DESCRIPTION OF EMBODIMENTS

Figure 1:
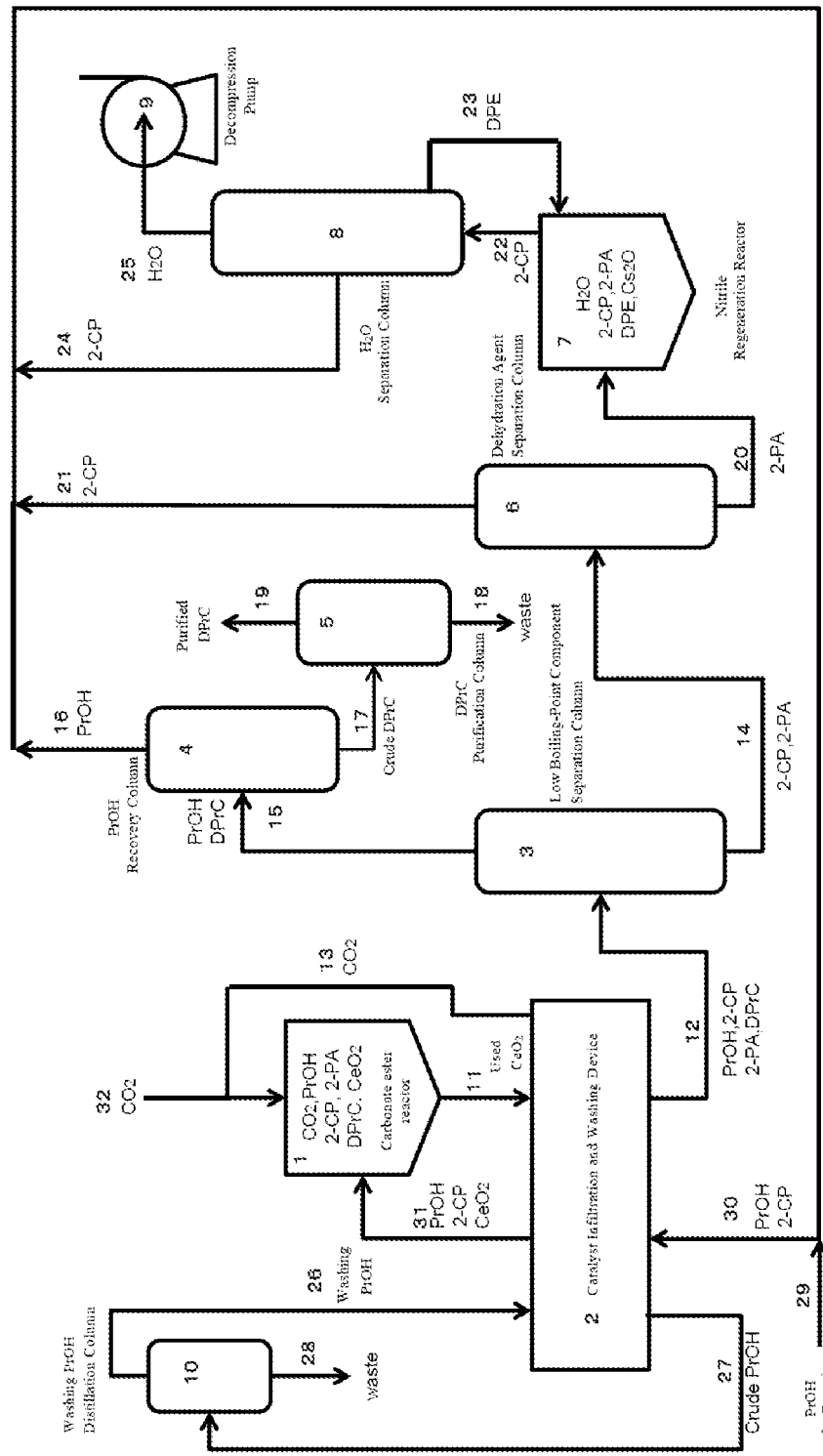
FIG. 1 shows an example of a carbonate ester production device.

Hereinafter, a preferable embodiment of the present invention will be described in detail with reference to the attached drawings. In the specification and the drawings, components having substantially the same functions or structures will bear the same reference signs, and the same descriptions will not be repeated.

<1. Method for Producing a Carbonate Ester>

A method according to the present invention for producing a carbonate ester includes a carbonate ester generation reaction of generating a carbonate ester from carbon dioxide and an alcohol. For the carbonate ester generation reaction, a purified catalyst obtained as a result of a used catalyst being regenerated is used as described below in detail. Hereinafter, such a method for producing a carbonate ester will be described.

(Carbonate Ester Generation Reaction)

The method according to the present invention for producing a carbonate ester includes a step of causing a reaction of directly reacting an alcohol and carbon dioxide with each other under the presence of a solid catalyst containing $CeO_2$ (cerium oxide) (carbonate ester generation reaction) to obtain a carbonate ester. A specific example of the carbonate ester generation reaction in which methanol is used is represented by the following formula (1)

[Chemical formula 1]

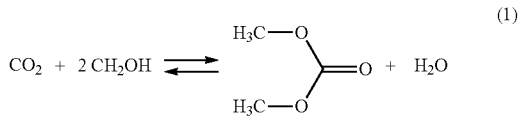

(1)

(Alcohol in the Carbonate Ester Generation Reaction)

An alcohol usable for the carbonate ester generation reaction may be any one, or two or more, selected from primary alcohol, secondary alcohol and tertiary alcohol. Examples of such an alcohol include methanol, ethanol, 1-propanol, isopropanol (2-propanol), 1-butanol, 2-butanol, isobutylalcohol, tert-butylalcohol, 1-pentanol, 1-hexanol, 1-heptanol, 1-octanol, 1-nonanol, allyl alcohol, 2-methyl-1-propanol, cyclohexanemethanol, benzylalcohol, ethyleneglycol, 1,2-propanediol, and 1,3-propanediol. These alcohols increase the yield of the product and also increase the reaction speed, and therefore are preferable. The carbonate esters generated by use of the above-listed alcohols are respectively dimethyl carbonate, diethyl carbonate, dipropyl carbonate, diisopropyl carbonate, dibutyl carbonate, dipentyl carbonate, dihexyl carbonate, diheptyl carbonate, dioctyl carbonate, dinonane carbonate, diallyl carbonate, di-2-methyl-propyl carbonate, dicyclohexanemethyl carbonate, dibenzyl carbonate, ethylene carbonate, 1,2-propylene carbonate, and 1,3-propylene carbonate.

In the case where the carbonate ester obtained by the carbonate ester generation reaction is used as a material of diaryl carbonate, it is preferable to use an alcohol having a carbon number of 1 to 6, and it is more preferable to use an alcohol having a carbon number of 1 to 4, for example, propanol or butanol, among the above-listed specific examples. It is preferable to use a monohydric or dihydric alcohol.

(Catalyst Usable for Producing a Carbonate Ester)

For the carbonate ester generation reaction, a catalyst containing $CeO_2$ as an activation component is used. A catalyst containing $ZrO_2$, $ReO_2$, $NiO$, $Al_2O_3$, $Y_2O_3$ or the like as a component other than $CeO_2$ is usable. A preferable catalyst usable for the carbonate ester generation reaction is a solid catalyst containing, for example, only $CeO_2$, a mixture of $CeO_2$ and $ZrO_2$, a solid solution of $CeO_2$ and $ZrO_2$, or a composite oxide of $CeO_2$ and $ZrO_2$, or the like. It is especially preferable to use a solid catalyst containing only $CeO_2$ as an activation component. The mixing ratio of $CeO_2$ and $ZrO_2$ in the solid solution or the composite oxide is basically 50:50, but may be changed appropriately.

The catalyst usable for the carbonate ester generation reaction may be in the form of powder or a molded body. In consideration of the activity, it is preferable that the catalyst is powder. By contrast, in consideration of the infiltration step and the separation step, it is preferable that the catalyst is a molded body. In the case of being a molded body, the catalyst may be spherical, pellet-like, cylindrical, ring-shaped, wheel-shaped, granular or the like.

A catalyst containing $CeO_2$ or the like as an activation component carried by a carrier may be used. For example, a catalyst containing an activation component carried by one or two among $SiO_2$, $ZrO_2$, $Al_2O_3$, $TiO_2$, activated carbon, zeolite and the like as a carrier may be used.

The catalyst has an average particle diameter of preferably 0.01 to 200 μm, more preferably 1 to 100 μm, and especially preferably 5 to 50 μm. The catalyst has a specific surface area of preferably 50 to 200 $m^2/g$, more preferably 70 to 200 $m^2/g$, and especially preferably 100 to 200 $m^2/g$.

The average particle diameter of a solid catalyst is a value defined in conformity to JIS Z 8825:2013. The specific surface area of a solid catalyst is a value defined in conformity to JIS Z 8830.

The above-mentioned numerical value ranges of the average particle diameter and the specific surface area are for particles substantially containing only an activation component such as $CeO_2$ or the like, for example, particles containing an activation component at a content of 99% by weight or higher. In the case where the catalyst includes a carrier or a molded body, the above-mentioned numerical value ranges of the average particle diameter and the specific surface area are not for particles including the carrier or the molded body. In the case where the catalyst contains a carrier or a molded body, it is preferable that particles of an activation component used to produce the catalyst has an average particle diameter and a specific surface area in the above-described numerical value ranges.

In the case where the catalyst contains a component other than the activation component, for example, a component such as a carrier or a molded body, the catalyst contains an activation component at a content of preferably at least 50% by weight, more preferably at least 70% by weight, and especially preferably at least 90% by weight.

(Carbon Dioxide)

In the present invention, carbon dioxide prepared as industrial gas, or carbon dioxide separated and recovered from exhaust gas of plants producing various products, steel manufacturing plants, power plants or the like, is usable.

(Use of a Solvent in the Carbonate Ester Generation Reaction)

In the carbonate ester generation reaction, the catalyst is powder. Therefore, the catalyst and the reaction system are easily separated from each other by an operation such as infiltration or the like. This makes it unnecessary to perform solid-liquid separation by distillation. For this reason, it is not necessary to use a solvent. Since neither the carbonate ester generation reaction nor the method for producing a carbonate ester including the carbonate ester generation reaction uses a solvent as described above, the number of types of components required in the reaction system may be minimized. It should be noted that a solvent may be used for the carbonate ester generation reaction. An example of solvent usable for the carbonate ester generation reaction is either one of dialkylbenzene, alkylnaphthalene, diphenylbenzene and the like.

(Hydration Step)

When an alcohol and carbon dioxide are reacted with each other in the carbonate ester generation reaction as shown in chemical formula (1), water is generated in addition to the carbonate ester. Therefore, it is preferable to remove water from the reaction system in order to efficiently generate the carbonate ester by the equilibrium reaction shown in chemical formula (1). For this purpose, it is preferable to incorporate a nitrile compound, preferably, an aromatic nitrile compound, into the reaction system, to generate an amide compound by a hydration reaction of the nitrile compound with water, and to remove the generated water from the reaction system.

As described above, a hydration step of hydrating the aromatic nitrile compound with water, which is a by-product, to generate an aromatic amide compound may be used. In this case, water is efficiently removed from the reaction system, and thus the generation of the carbonate ester may be promoted. This is expressed by, for example, the following chemical formula (2).

[Chemical formula 2]

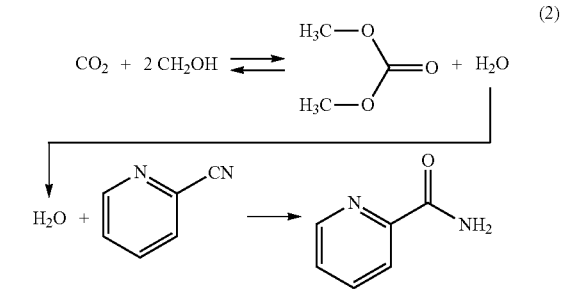

(Step of Regenerating a Nitrile Compound)

As shown in chemical formula (2), the aromatic amide compound is generated as a by-product as a result of the hydration step. Preferably, the aromatic amide compound thus generated as a by-product is separated from the system, preferably after the carbonate ester generation reaction, and then is dehydrated, to regenerate the aromatic nitrile compound. The regenerated aromatic nitrile compound is reusable for the above-described hydration step.

An example of method for generating (regenerating) the aromatic nitrile compound is a reaction, expressed by the following chemical formula (3), which is caused with a catalyst containing a basic metal oxide such as $Cs_2O$ or the like in the presence of a predetermined catalyst. In this reaction, 2-picolinamide, which is an aromatic amide compound, is converted into 2-cyanopyridine, which is an aromatic nitrile compound, by a dehydration reaction.

[Chemical formula 3]

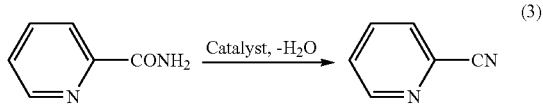

The catalyst usable in the dehydration reaction according to the present invention contains an oxide of an alkaline metal (K, Li, Na, Pb, Cs), which is to become basic. For the above-described reaction, it is especially preferable to use a catalyst containing an oxide of at least one of Na, K, Rb and Cs (cesium). As a carrier for the catalyst, a substance that is commonly used as a carrier is usable. As a result of examining various carriers, it has been found out that a catalyst carried by one or two among $SiO_2$ and $ZrO_2$ is preferably usable.

<2. Regeneration of a Catalyst for the Carbonate Ester Generation Reaction>
(Crude Catalyst Separation Step)

When the above-described carbonate ester generation reaction is continued, the activity of the catalyst is decreased. Therefore, according to the present invention, a used catalyst is separated and recovered, and then is regenerated. As can be seen, according to the method for regenerating a catalyst of the present invention, first, a catalyst that has been used for at least a certain time period is separated as a crude catalyst from a reaction solution (reaction system) of carbon dioxide and an alcohol by a technique such as infiltration, centrifugation or the like.

(Catalyst Processing Step)

The crude catalyst separated by the separation step is washed with a washing solution containing at least a washing alcohol. Such a catalyst that is obtained as a result of the crude catalyst being washed and has the activity thereof recovered is used again as a purified catalyst for the carbonate ester generation reaction.

(Washing Alcohol Usable for the Catalyst Processing Step)

A preferable washing alcohol to be used for the catalyst processing step contains the same type of alcohol as used for the carbonate ester generation reaction. In the case where the same type of alcohol is selected as the alcohol for the carbonate ester generation reaction and as the washing alcohol as described above, the washing alcohol remaining in the purified catalyst may be reused for the carbonate ester generation reaction with no need to be completely removed after the catalyst processing step. More preferably, the washing alcohol contains only the same type of alcohol as used for the carbonate ester generation reaction.

Examples of alcohol usable as the washing alcohol include methanol, ethanol, 1-propanol, isopropanol (2-propanol), 1-butanol, 2-butanol, isobutylalcohol, tert-butylalcohol, 1-pentanol, 1-hexanol, 1-heptanol, 1-octanol, 1-nonanol, allylalcohol, 2-methyl-1-propanol, cyclohexanemethanol, benzylalcohol, ethyleneglycol, 1,2-propanediol, and 1,3-propanediol.

Among the above-listed specific examples, it is preferable to use an alcohol having a carbon number of 1 to 6, and it is more preferable to use an alcohol having a carbon number of 1 to 4, for example, at least one of propanol and butanol. It is preferable to use a monohydric or dihydric alcohol.

(Conditions Under which the Crude Catalyst is Washed in the Catalyst Processing Step)

A preferable washing alcohol to be used for the catalyst processing step contains the same type of alcohol as used for the carbonate ester generation reaction. In the case where the same type of alcohol is selected as the alcohol for the carbonate ester generation reaction and as the washing alcohol as described above, the washing alcohol remaining in the purified catalyst may be reused for the carbonate ester generation reaction with no need to be completely removed after the catalyst processing step. More preferably, the washing alcohol contains only the same type of alcohol as used for the carbonate ester generation reaction.

In the catalyst processing step, the crude catalyst is washed at preferably 0 to 150° C., more preferably 15 to 120° C., and especially preferably 15 to 100° C. It is especially preferable to wash the crude catalyst at room temperature because in this case, no special device for adjusting the temperature is needed. In this specification, the room temperature is 15 to 40° C. It should be noted that the temperature at which the catalyst is washed may be appropriately adjusted in accordance with, for example, the type of the washing alcohol to be used.

The molar ratio of the washing alcohol (or the above-mentioned washing solution) with respect to the crude catalyst to be washed in the catalyst processing step (molar number of the activation component of the crude catalyst/molar number of the washing alcohol (or the washing solution) is preferably 1.5 to 10000, more preferably 100 to 10000, and especially preferably 1000 to 10000.

In the catalyst processing step, the crude catalyst is washed for a time period in the range of, for example, 1 second to 600 minutes, more preferably of 1 to 60 minutes, and especially preferably of 1 to 30 minutes.

(Recovery Step)

Preferably, the method for regenerating a catalyst of the present invention includes a step of recovering the washing alcohol (or the washing solution). In the case where the recovery step is adopted, the washing alcohol once used may be used again for the catalyst processing step or the carbonate ester generation reaction.

(Reuse of the Purified Catalyst)

According to the present invention, as described below in detail, use of merely the washing alcohol for washing the crude catalyst in the catalyst processing step allows the activity of the catalyst to be sufficiently restored. Therefore, no special device for a step of calcining or the like is needed, and the crude catalyst may be reused as a purified catalyst by a simple technique.

It should be noted that the crude catalyst may be calcined in addition to be washed according to the present invention.

<3. Carbonate Ester Production Device>

Figure 2:
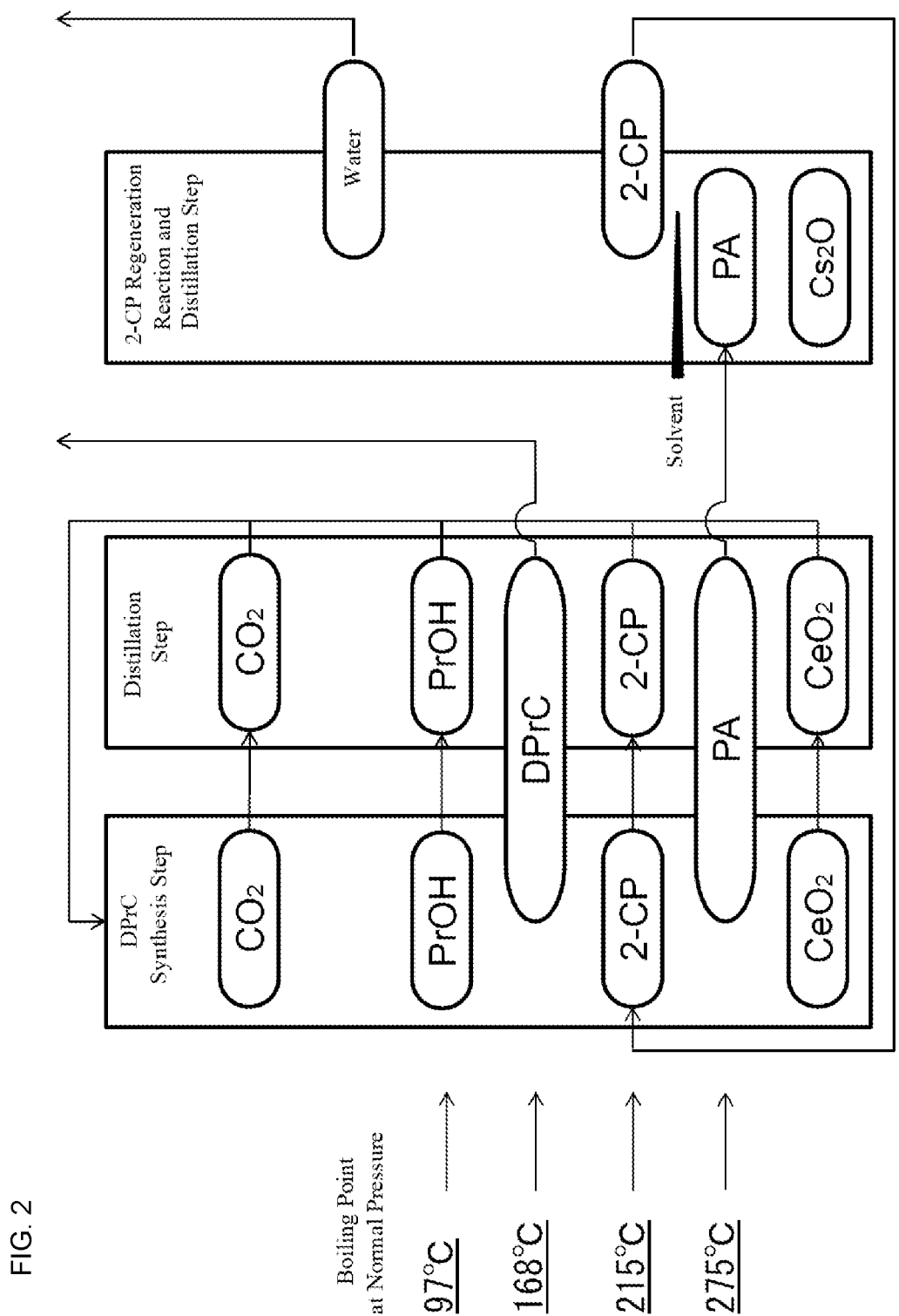
FIG. 2 is a chart showing the state of each of substances in each of steps performed by use of the production device shown in FIG. 1.

Now, a production device usable in the present invention will be described in detail by way of a specific example. FIG. 1 shows an example of preferable facilities for producing a carbonate ester. FIG. 2 schematically shows the state of each of substances in each of steps performed by use of the facilities shown in FIG. 1.

(Carbonate Ester Generation Reaction)

In the carbonate ester generation reaction, a carbonate ester reactor 1 is filled with a solid catalyst (solid phase) containing $CeO_2$ as a main component, alcohol (1-propanol (PrOH); liquid phase), 2-cyanopyridine (2-CP; liquid phase), and carbon dioxide ($CO_2$: gas phase) supplied via a pressure raising blower (not shown). The solid catalyst ($CeO_2$; solid phase) may be newly supplied before the reaction or recovered from a catalyst infiltration and washing device 2. New 2-cyanopyridine is used at the start of the reaction. Alternatively, 2-cyanopyridine 21 (gas phase) separated and purified in a dehydration agent separation column 6, and 2-cyanopyridine 24 (liquid phase) regenerated from 2-picolinamide purified in a water separation column 8, are reusable.

In a direct synthesis device for a carbonate ester shown in FIG. 1, a solid catalyst containing $CeO_2$ is used. The synthesis device may be a flow reactor such as a batch reactor, a semi-batch reactor, a continuous tank reactor, a tube reactor or the like.

(Temperature of the Reaction Solution)

The temperature of the reaction solution in the carbonate ester reactor 1 is preferably 50 to 300° C. In the case where the temperature of the reaction solution is lower than 50° C., the reaction speed is low, and neither the carbonate ester synthesis reaction nor the hydration reaction with 2-cyanopyridine advances almost at all. In this case, the productivity of the carbonate ester tends to be low. In the case where the temperature of the reaction solution is higher than 300° C., the reaction speed of each reaction is high, but the carbonate ester is easily decomposed or denatured and 2-picolinamide is easily reacted with an alcohol. Therefore, the yield of the carbonate ester tends to be low. The temperature of the reaction solution is more preferably 100 to 150° C. An ideal temperature of the reaction solution is considered to vary in accordance with the type or the amount of the solid catalyst, or the amount or the ratio of the materials (alcohol and 2-cyanopyridine). Thus, it is desirable to set the optimal temperature appropriately. Since the preferable temperature of the reaction solution is 100 to 150° C., it is desirable to pre-heat the materials (alcohol and 2-cyanopyridine) with steam or the like on a stage before the carbonate ester reactor.

(Reaction Pressure)

The reaction pressure in the carbonate ester reactor 1 is preferably 0.1 to 20 MPa (absolute pressure). In the case where the reaction pressure is lower than 0.1 MPa (absolute pressure), a decompression device is required, which makes the facilities complicated and costly. In addition, a motive power energy to reduce the pressure is necessary, which decreases the energy efficiency. In the case where the reaction pressure is higher than 20 MPa, the hydration reaction with 2-cyanopyridine does not easily advance, which decreases the yield of the carbonate ester. In addition, a motive power energy to raise the pressure is necessary, which decreases the energy efficiency. From the point of view of increasing the yield of the carbonate ester, the reaction pressure is more preferably 0.5 to 15 MPa (absolute pressure), and still more preferably 1.0 to 10 MPa (absolute pressure).

(Separation of the Crude Catalyst)

In the carbonate ester reactor 1, the $CeO_2$ catalyst, after being used for the generation of the carbonate ester for at least a certain time period, is separated from the reaction system by infiltration and is transmitted to the catalyst infiltration and washing device 2 as a used crude catalyst 11.

The catalyst infiltration and washing device 2 is supplied with washing PrOH 26 from a washing PrOH distillation column 10, and the crude catalyst 11 is washed with the washing PrOH. Crude PrOH 27 used to wash the crude catalyst 11 is transmitted to the washing PrOH distillation column 10. In the washing PrOH distillation column 10, the crude PrOH 27 is purified and reused as the washing PrOH 26. A part of the crude PrOH 27 is discarded as waste 28.

The reaction solution after the reaction is transmitted from the carbonate ester reactor 1 to the catalyst infiltration and washing device 2 together with the used crude catalyst 11. From a top of the catalyst infiltration and washing device 2, $CO_2$ 13, PrOH, 2-cyanopyridine and a post-washing $CeO_2$ catalyst 31 are recovered and transmitted to the carbonate ester reactor 1 to be recycled.

A mixture 12 recovered from the catalyst infiltration and washing device 2, namely, the mixture 12 of PrOH, 2-cyanopyridine, 2-picolinamide and DPrC (dipropyl carbonate), which is a target compound, is transmitted to a low boiling-point component separation column 3. From a bottom of the low boiling-point component separation column 3, a mixture 14 of 2-cyanopyridine and 2-picolinamide is recovered. From a top of the low boiling-point component separation column 3, PrOH and DPrC (dipropyl carbonate) 15 are recovered.

The mixture 14 recovered from the bottom of the low boiling-point component separation column 3 is transmitted to a dehydration agent separation column 6. From a bottom of the dehydration agent separation column, 2-picolinamide 20 is recovered. From a top of the dehydration agent separation column, the 2-cyanopyridine 21 is recovered. The recovered 2-cyanopyridine 21 is recycled to the carbonate ester reactor 1. The 2-picolinamide 20 recovered from the bottom of the dehydration agent separation column 6 is transmitted to a nitrile regeneration reactor 7.

The PrOH and the DPrC 15 recovered from the top of the low boiling-point component separation column 3 are transmitted to an alcohol (PrOH) recovery column 4, and crude DPrC (crude dipropyl carbonate) 17 is recovered from a bottom of the alcohol recovery column 4. The crude DPrC 17 is transmitted to a DPrC (dipropyl carbonate) purification column 5. In the meantime, PrOH 16 is recovered from a top of the alcohol recovery column 4. The recovered PrOH is recycled to the carbonate ester reactor 1.

In the DPrC purification column 5, the crude DPrC 17 is purified. The obtained purified DPrC 19 is recovered as a final target compound. In the meantime, impurities and the like are discarded as the waste 18.

The 2-picolinamide (2-PA; 20) recovered by the dehydration agent separation column 6 is transferred to the nitrile regeneration reactor 7 in order to be regenerated into 2-cyanopyridine. In the nitrile regeneration reactor 7, a dehydration reaction of the 2-picolinamide is caused under the presence of a catalyst containing $Cs_2O$ and diphenylether (DPE) as a solvent, and as a result, 2-cyanopyridine (2-CP) is generated.

2-cyanopyridine 22 may be recovered from the nitrile regeneration reactor 7 during the reaction, or may be distilled and recovered as it is after the reaction. The recovered 2-cyanopyridine 22 is transmitted to a water separation column 8 together with a part of the DPE as the solvent. 2-cyanopyridine 24 recovered and purified in the water separation column 8 is transmitted to the carbonate ester reactor 1 as described above and is reused to produce the carbonate ester. In the meantime, DPE 23, which is the solvent and recovered by the water separation column 8, is recycled to the nitrile regeneration reactor 7.

In the above-described embodiment of the present invention, the catalyst used to produce dipropyl carbonate (DPrC), which is a carbonate ester, may be regenerated by a simple technique of washing the catalyst with a washing alcohol of the same type as the alcohol (PrOH) used to produce DPrC.

EXAMPLES

Hereinafter, the present invention will be described in more detail by way of examples. The present invention is not limited to any of the following examples. First, examples and comparative examples of method for producing a carbonate ester will be described. In the examples, a regenerated catalyst is used, and in the comparative examples, an unregenerated catalyst is used.

In example 1 through 4, a carbonate ester was produced by use of a regenerated catalyst.

Example 1

First, cerium oxide (impurity concentration: 0.02% or lower) was calcined at 600° C. for 3 hours in an air atmosphere to obtain a powdery solid catalyst. The solid catalyst thus obtained had an average particle diameter of about 10 μm and a specific surface area of about 120 $cm^2/g$.

The average particle diameter of the solid catalyst was measured by use of the laser diffraction/scattering particle size distribution meter LA-920 produced by Horiba, Ltd. in conformity to JIS Z 8825:2013. The specific surface area of the solid catalyst was measured by a BET multi-point method with nitrogen gas by use of the GEMINI 2360 produced by Shimadzu Corporation in conformity to JIS Z 8830.

Next, the above-described catalyst, a dehydration agent and a matrix (1-butanol) were incorporated into an autoclave (table autoclave Start 200 produced by Nitto Koatsu Kabushiki Kaisha). After $CO_2$ substitution, the system was filled with $CO_2$, and a reaction was caused under predetermined conditions (reaction pressure: 8 MPa; reaction temperature: 132° C., reaction time: 4 hours) (carbonate ester generation reaction). Then, the autoclave was cooled down. After depressurization was performed, the reaction solution was recovered. 2-picolinamide had been deposited as a by-product. Therefore, the deposited 2-picolinamide was washed together with the catalyst with an alcohol, as a washing solvent, of the same type as the above-mentioned matrix, while the reaction solution was recovered into a sample bottle.

Then, the reaction solution was heated in a water bath of 55° C. to dissolve the 2-picolinamide in the solution. Then, the components in the reaction solution were subjected to GC measurement, and the reaction solution was absorbed and thus infiltrated to recover the catalyst.

The catalyst thus recovered was washed at room temperature with an alcohol, as a washing solvent, of the same type as the above-mentioned matrix, while being stirred for 10 minutes by a stirrer (250 mmol of the washing solvent with respect to 7.5 mmol of the catalyst). The washing solution was absorbed and thus infiltrated to recover the catalyst. The above-described washing with the alcohol as the washing solvent was performed again. The washing solution was absorbed and thus infiltrated to recover the catalyst again, and the catalyst was dried at room temperature at a reduced pressure (100 Pa or lower).

The dried catalyst (purified catalyst) thus obtained, the dehydration agent and the matrix (alcohol) were incorporated again as described above. After $CO_2$ substitution, the system was filled with $CO_2$. In this manner, the carbonate ester generation reaction was repeated.

In each of examples 2, 3 and 4, the same operation as in example 1 was performed except that the type of the alcohol used as the matrix was changed from that used in example 1. In each of examples 1 through 4, the above-described carbonate ester generation reaction was repeated four times. The results of examples 1 through 4 are shown in Table 1 and Table 2. Table 1 and Table 2 include the results of the first through fourth cycles (the first carbonate ester generation reaction through the fourth carbonate ester generation reaction) in each of examples 1 through 4 as described in the footnote.

TABLE 1

| | WASHING SOLVENT | MATRIX | AMOUNT OF MATRIX [mmol] | DEHYDRATION AGENT | AMOUNT OF DEHYDRATION AGENT [mmol] | CATALYST | AMOUNT OF CATALYST [mmol] | REACTION PRESSURE [MPa] |
|---|---|---|---|---|---|---|---|---|
| EX. 1 | BuOH | BuOH | 250 | 2-CYANO-PYRIDINE | 125 | $CeO_2$ | 2.5 | 8 |
| EX. 2 | PrOH | PrOH | 250 | 2-CYANO-PYRIDINE | 125 | $CeO_2$ | 2.5 | 8 |
| EX. 3 | EtOH | EtOH | 250 | 2-CYANO-PYRIDINE | 125 | $CeO_2$ | 2.5 | 8 |
| EX. 4 | MeOH | MeOH | 250 | 2-CYANO-PYRIDINE | 125 | $CeO_2$ | 2.5 | 8 |

| | REACTION TEMPERATURE [° C.] | REACTION TIME [h] | PRODUCT | ALCOHOL CONVERSION RATIO [mol %](*) 1 | 2 | 3 | 4 | PRODUCT YIELD [mol %](*) 1 | 2 | 3 | 4 | DECREASE RATIO |
|---|---|---|---|---|---|---|---|---|---|---|---|---|
| EX. 1 | 132 | 4 | DBC | 45% | 42% | 42% | 42% | 45% | 42% | 42% | 42% | 6.7% |
| EX. 2 | 132 | 4 | DPrC | 54% | 51% | 51% | 51% | 54% | 50% | 50% | 50% | 6.7% |
| EX. 3 | 132 | 4 | DEC | 74% | 69% | 69% | 69% | 71% | 66% | 66% | 66% | 6.6% |
| EX. 4 | 132 | 4 | DMC | 87% | 81% | 81% | 81% | 83% | 78% | 78% | 78% | 6.6% |

(*)The numerical values "1" through "4" regarding the alcohol conversion ratio and the product yield respectively represent the first cycle through the fourth cycle.

TABLE 2

| | WASHING SOLVENT | MATRIX | AMOUNT OF MATRIX [mmol] | DEHYDRATION AGENT | AMOUNT OF DEHYDRATION AGENT [mmol] | CATALYST | AMOUNT OF CATALYST [mmol] | REACTION PRESSURE [MPa] |
|---|---|---|---|---|---|---|---|---|
| EX. 1 | BuOH | BuOH | 250 | 2-CYANO-PYRIDINE | 125 | $CeO_2$ | 2.5 | 8 |
| EX. 2 | PrOH | PrOH | 250 | 2-CYANO-PYRIDINE | 125 | $CeO_2$ | 2.5 | 8 |
| EX. 3 | EtOH | EtOH | 250 | 2-CYANO-PYRIDINE | 125 | $CeO_2$ | 2.5 | 8 |
| EX. 4 | MeOH | MeOH | 250 | 2-CYANO-PYRIDINE | 125 | $CeO_2$ | 2.5 | 8 |

TABLE 2-continued

| | REACTION TEMPERATURE [° C.] | REACTION TIME [h] | PRODUCT | YIELD OF ALKYL PICOLINATE [mol %](*) | | | | YIELD OF ALKYL PICOLINIMIDATE [mol %](*) | |
|---|---|---|---|---|---|---|---|---|---|
| | | | | 1 | 2 | 3 | 4 | 1 | 2 |
| EX. 1 | 132 | 4 | DBC | 0.26% | 0.28% | 0.28% | 0.27% | 0.04% | 0.04% |
| EX. 2 | 132 | 4 | DPrC | 0.22% | 0.21% | 0.19% | 0.22% | 0.08% | 0.07% |
| EX. 3 | 132 | 4 | DEC | 0.37% | 0.38% | 0.37% | 0.37% | 0.10% | 0.11% |
| EX. 4 | 132 | 4 | DMC | 0.70% | 0.68% | 0.69% | 0.70% | 0.24% | 0.24% |

| | YIELD OF ALKYL PICOLINIMIDATE [mol %](*) | | YIELD OF ALKYL CARBAMATE [mol %] | | | |
|---|---|---|---|---|---|---|
| | 3 | 4 | 1 | 2 | 3 | 4 |
| EX. 1 | 0.05% | 0.07% | BELOW DETECTION LIMIT | BELOW DETECTION LIMIT | BELOW DETECTION LIMIT | BELOW DETECTION LIMIT |
| EX. 2 | 0.08% | 0.08% | 0.30% | 0.26% | 0.27% | 0.26% |
| EX. 3 | 0.10% | 0.11% | 0.57% | 0.53% | 0.55% | 0.54% |
| EX. 4 | 0.25% | 0.26% | 1.29% | 1.28% | 1.26% | 1.28% |

(*)The numerical values "1" through "4" regarding the yield of alkyl picolinate, the yield of picolinimidate and the yield of alkyl carbamate respectively represent the first cycle though the fourth cycle.

In comparative examples 1 through 4, carbonate ester generation reactions were caused by use of alcohols respectively corresponding to those in examples 1 through 4 and an unwashed, unregenerated catalyst.

Comparative Example 1

First, like in example 1, the first carbonate ester generation reaction was caused to proceed. Then, the autoclave was cooled down. After depressurization, the deposited 2-picolinamide was dropped into a pot (reactor) with the matrix (alcohol) with no washing of the catalyst. Then, the lid of the reactor was replaced, and the reaction solution was distilled to be removed. The components of the removed reaction solution were analyzed by GC measurement. The catalyst remaining in the pot (reactor) was used without being washed to repeat the carbonate ester generation reaction.

In each of comparative examples 2, 3 and 4, the same operation as in comparative example 1 was performed except that the type of the alcohol used as the matrix was changed from that used in comparative example 1. In each of comparative examples 1 through 4, the above-described carbonate ester generation reaction was repeated four times like in examples 1 through 4. The results of comparative examples 1 through 4 are shown in Table 3 and Table 4. Table 3 and Table 4 include the results of the first through fourth cycles (the first carbonate ester generation reaction through the fourth carbonate ester generation reaction) in each of comparative examples 1 through 4 as described in the footnote.

TABLE 3

| | WASHING SOLVENT | MATRIX | AMOUNT OF MATRIX [mmol] | DEHYDRATION AGENT | AMOUNT OF DEHYDRATION AGENT [mmol] | CATALYST | AMOUNT OF CATALYST [mmol] | REACTION PRESSURE [MPa] |
|---|---|---|---|---|---|---|---|---|
| COMPARATIVE EX. 1 | — | BuOH | 250 | 2-CYANOPYRIDINE | 125 | CeO2 | 2.5 | 8 |
| COMPARATIVE EX. 2 | — | PrOH | 250 | 2-CYANOPYRIDINE | 125 | CeO2 | 2.5 | 8 |
| COMPARATIVE EX. 3 | — | EtOH | 250 | 2-CYANOPYRIDINE | 125 | CeO2 | 2.5 | 8 |
| COMPARATIVE EX. 4 | — | MeOH | 250 | 2-CYANOPYRIDINE | 125 | CeO2 | 2.5 | 8 |

| | REACTION TEMPERATURE [° C.] | REACTION TIME [h] | PRODUCT | ALCOHOL CONVERSION RATIO [mol %](*) | | | | PRODUCT YIELD [mol %](*) | | | | DECREASE RATIO |
|---|---|---|---|---|---|---|---|---|---|---|---|---|
| | | | | 1 | 2 | 3 | 4 | 1 | 2 | 3 | 4 | |
| COMPARATIVE EX. 1 | 132 | 4 | DBC | 43% | 36% | 32% | 23% | 42% | 35% | 31% | 22% | 47.6% |
| COMPARATIVE EX. 2 | 132 | 4 | DPrC | 50% | 45% | 41% | 40% | 50% | 44% | 40% | 38% | 23.2% |
| COMPARATIVE EX. 3 | 132 | 4 | DEC | 71% | 66% | 61% | 57% | 68% | 63% | 58% | 53% | 22.1% |
| COMPARATIVE EX. 4 | 132 | 4 | DMC | 85% | 80% | 74% | 69% | 80% | 75% | 70% | 65% | 19.0% |

(*)The numerical values "1" through "4" regarding the alcohol conversion ratio and the product yield respectively represent the first cycle through the fourth cycle.

TABLE 4

| | WASHING SOLVENT | MATRIX | AMOUNT OF MATRIX [mmol] | DEHYDRATION AGENT | AMOUNT OF DEHYDRATION AGENT [mmol] | CATALYST | AMOUNT OF CATALYST [mmol] | REACTION PRESSURE [MPa] |
|---|---|---|---|---|---|---|---|---|
| COMPARATIVE EX. 1 | — | BuOH | 250 | 2-CYANO-PYRIDINE | 125 | CeO2 | 2.5 | 8 |
| COMPARATIVE EX. 2 | — | PrOH | 250 | 2-CYANO-PYRIDINE | 125 | CeO2 | 2.5 | 8 |
| COMPARATIVE EX. 3 | — | EtOH | 250 | 2-CYANO-PYRIDINE | 125 | CeO2 | 2.5 | 8 |
| COMPARATIVE EX. 4 | — | MeOH | 250 | 2-CYANO-PYRIDINE | 125 | CeO2 | 2.5 | 8 |

| | REACTION TEMPERATURE [°C.] | REACTION TIME [h] | PRODUCT | YIELD OF ALKYL PICOLINATE [mol %](*) | | | | YIELD OF ALKYL PICOLINIMIDATE [mol %](*) | |
|---|---|---|---|---|---|---|---|---|---|
| | | | | 1 | 2 | 3 | 4 | 1 | 2 |
| COMPARATIVE EX. 1 | 132 | 4 | DBC | 0.24% | 0.29% | 0.35% | 0.36% | 0.23% | 0.32% |
| COMPARATIVE EX. 2 | 132 | 4 | DPrC | 0.20% | 0.22% | 0.30% | 0.40% | 0.14% | 0.28% |
| COMPARATIVE EX. 3 | 132 | 4 | DEC | 0.35% | 0.37% | 0.43% | 0.48% | 0.28% | 0.44% |
| COMPARATIVE EX. 4 | 132 | 4 | DMC | 0.66% | 0.69% | 0.72% | 0.76% | 0.40% | 0.55% |

| | YIELD OF ALKYL PICOLINIMIDATE [mol %](*) | | YIELD OF ALKYL CARBAMATE [mol %] | | | |
|---|---|---|---|---|---|---|
| | 3 | 4 | 1 | 2 | 3 | 4 |
| COMPARATIVE EX. 1 | 0.55% | 0.29% | BELOW DETECTION LIMIT | BELOW DETECTION LIMIT | BELOW DETECTION LIMIT | BELOW DETECTION LIMIT |
| COMPARATIVE EX. 2 | 0.64% | 1.07% | 0.24% | 0.26% | 0.36% | 0.46% |
| COMPARATIVE EX. 3 | 0.87% | 1.35% | 0.53% | 0.57% | 0.63% | 0.69% |
| COMPARATIVE EX. 4 | 1.10% | 1.46% | 1.20% | 1.23% | 1.30% | 1.32% |

(*)The numerical values "1" through "4" regarding the yield of alkyl picolinate, the yield of alkyl picolinimidate and the yield of alkyl carbamate respectively represent the first cycle through the fourth cycle.

In example 5, the same operation as in example 2 was performed except that the amount of the washing alcohol was decreased.

Example 5

In example 2, after each cycle of the carbonate ester generation reaction, the washing solvent was used in an amount of 250 mmol for 7.5 mmol of the recovered catalyst. In example 5, the washing solvent was used in an amount of merely 8.3 mmol for 5 mmol of the recovered catalyst. Example 5 is different from example 2 only on this point. The results of example 5 are shown in Table 5 together with the results of example 2 and comparative example 2.

TABLE 5

| | WASHING SOLVENT | MATRIX | AMOUNT OF MATRIX [mmol] | DEHYDRATION AGENT | AMOUNT OF DEHYDRATION AGENT [mmol] | CATALYST | AMOUNT OF CATALYST [mmol] | REACTION PRESSURE [MPa] |
|---|---|---|---|---|---|---|---|---|
| EX. 2 | PrOH | PrOH | 250 | 2-CYANO PYRIDINE | 125 | CeO2 | 2.5 | 8 |
| EX. 5 | PrOH | PrOH | 250 | 2-CYANO PYRIDINE | 125 | CeO2 | 2.5 | 8 |
| COMPARATIVE EX. 2 | — | PrOH | 250 | 2-CYANO PYRIDINE | 125 | CeO2 | 2.5 | 8 |

TABLE 5-continued

| | REACTION TEMPERATURE [° C.] | REACTION TIME [h] | PRODUCT | WASHING SOLVENT/ CATALYST MOLAR RATIO | ALCOHOL CONVERSION RATIO [mol %] | | PRODUCT YIELD [mol %] | | YIELD DECREASE RATIO AT 2ND CYCLE |
|---|---|---|---|---|---|---|---|---|---|
| | | | | | 1 | 2 | 1 | 2 | |
| EX. 2 | 132 | 4 | DPrC | 33.3 | 54% | 51% | 54% | 50% | 6.5% |
| EX. 5 | 132 | 4 | DPrC | 1.66 | 54% | 51% | 53% | 50% | 6.5% |
| COMPAR- TIVE EX. 2 | 132 | 4 | DPrC | 0 | 50% | 45% | 50% | 44% | 11.7% |

| | YIELD OF ALKYL PICOLINATE [mol %] | | YIELD OF ALKYL PICOLINIMIDATE [mol %] | | YIELD OF ALKYL CARBAMATE [mol %] | |
|---|---|---|---|---|---|---|
| | 1 | 2 | 1 | 2 | 1 | 2 |
| EX. 2 | 0.22% | 0.21% | 0.09% | 0.07% | 0.30% | 0.26% |
| EX. 5 | 0.22% | 0.21% | 0.09% | 0.07% | 0.30% | 0.24% |
| COMPAR- TIVE EX. 2 | 0.20% | 0.22% | 0.14% | 0.28% | 0.24% | 0.26% |

(*)The numerical values "1" through "4" regarding the alcohol conversion ratio, the product yield, the yield of alkyl picolinate, the yield of picolinimidate and the alkyl carbamate respectively represent the first cycle through the fourth cycle.

It has been conformed from above that in the examples in which the catalyst used for the carbonate ester generation reaction is reused again after being washed with the washing alcohol, the yield of the carbonate ester is kept at a higher level than in the comparative examples in which the washing step is skipped (see Table 1 and Table 3). It has also been confirmed that in the case where the catalyst is washed to be regenerated, the generation of a by-product is suppressed (see Table 2 and Table 4).

It has further been clarified that use of even a small amount of washing solvent with respect to the catalyst, which is a target of washing, has a large effect on the restoration of the activity of the catalyst (see Table 5).

Preferable embodiments of the present invention have been described above in detail with reference to the attached drawings. The present invention is not limited to any of the embodiments. A person of ordinary skill in the art of the present invention would obviously conceive any of various altered or modified examples within the scope of technological idea defined by the claims, and such altered or modified examples are construed as being duly encompassed in the technological scope of the present invention.

REFERENCE SIGNS LIST

1 Carbonate ester reactor
2 Catalyst infiltration and washing device
3 Low boiling-point separation column
4 PrOH recovery column
5 DPrC purification column
6 Dehydration agent separation column
7 Nitrile generation reactor
8 Water separation column
9 Decompression pump

The invention claimed is:

1. A method for regenerating a catalyst containing $CeO_2$, the catalyst being usable for a carbonate ester generation reaction of generating a carbonate ester from carbon dioxide and an alcohol, the method comprising:
(a) separating the catalyst as a crude catalyst from a reaction solution of carbon dioxide and the alcohol; and
(b) washing the crude catalyst with a washing alcohol to provide a purified catalyst, and
(c) recovering the washing alcohol used to wash the crude catalyst, wherein the recovered washing alcohol is used for the carbonate ester generation reaction.

2. The method for regenerating a catalyst according to claim 1, wherein the catalyst has an average particle diameter of 0.01 to 200 μm.

3. The method for regenerating a catalyst according to claim 1, wherein the catalyst has a specific surface area of 50 to 200 $m^2/g$.

4. The method for regenerating a catalyst according to claim 1, wherein the washing alcohol contains an alcohol of the same type as the alcohol used for the carbonate ester generation reaction.

5. The method for regenerating a catalyst according to claim 1, wherein the washing alcohol contains an alcohol having a carbon number of 1 to 4.

6. The method for regenerating a catalyst according to claim 5, wherein the washing alcohol contains at least one of propanol and butanol.

7. The method for regenerating a catalyst according to claim 1, wherein in (b), the crude catalyst is washed at 0 to 150° C.

8. The method for regenerating a catalyst according to claim 7, wherein in (b), the crude catalyst is washed at room temperature.

9. The method for regenerating a catalyst according to claim 1, wherein in (b), the washing alcohol is of a molar ratio of 1.5 to 10000 with respect to the crude catalyst to be washed.

10. The method for regenerating a catalyst according to claim 1, wherein in (b), the crude catalyst is washed for a time period in the range of 1 second to 600 minutes.

11. The method for regenerating a catalyst according to claim 1, wherein (b) further includes a step of calcining the washed crude catalyst.

12. A method for producing a carbonate ester, the method using the purified catalyst, regenerated by the method for regenerating a catalyst according to claim 1, for a carbonate ester generation reaction of generating a carbonate ester from carbon dioxide and an alcohol.

13. The method for producing a carbonate ester according to claim 12, further comprising:
(e) hydrating an aromatic nitrile compound with water generated in the carbonate ester generation reaction to generate an aromatic amide compound; and (f) dehydrating the aromatic amide compound to regenerate the aromatic nitrile compound.

14. The method for producing a carbonate ester according to claim 12, wherein the method uses no solvent.

* * * * *